United States Patent [19]

Parsons et al.

[11] 4,421,695

[45] Dec. 20, 1983

[54] PRODUCTION OF ALKOXYALKYL PHOSPHATE ESTERS

[75] Inventors: Norman C. Parsons, Winfield, W. Va.; Joseph H. Finley, Metuchen, N.J.

[73] Assignee: FMC Corporation, Philadelphia, Pa.

[21] Appl. No.: 366,265

[22] Filed: Apr. 7, 1982

[51] Int. Cl.³ ............................................... C07F 9/09
[52] U.S. Cl. .................................... 260/974; 260/950
[58] Field of Search ................ 568/621, 699; 260/974

[56] References Cited

U.S. PATENT DOCUMENTS 3,020,303  2/1962  Pianfetti et al. .................... 260/974
3,168,569  2/1965  Matell ................................ 568/621

FOREIGN PATENT DOCUMENTS 2457135  6/1975  Fed. Rep. of Germany ...... 568/621

*Primary Examiner*—Anton H. Sutto
*Attorney, Agent, or Firm*—Charles C. Fellows; Eugene G. Horsky

[57] ABSTRACT

A process for the production of alkoxyalkyl triorganic phosphates utilizing a continuous process for the manufacture of alkoxyalkyl alkoxides comprising treating an alkoxyalkanol with a sodium borohydride for 20 minutes to 4 hours reacting the treated alkoxyalkanol continuously with an alkali metal hydroxide to form an alkali metal alkoxide. A large excess of alcohol is employed. The alkoxide is phosphorylated to form a trialkoxyalkyl phosphate. The alkoxidation reaction and the phosphorylation reaction are both conducted in a nonoxidizing atmosphere. The crude product is then refined by conventional means.

4 Claims, No Drawings

PRODUCTION OF ALKOXYALKYL PHOSPHATE ESTERS

This invention relates to an improved process for the manufacture of alkoxyalkyl triorganic phosphates employing a continuous alkoxidation step.

Triorganic phosphates are generally made on a relatively small scale as compared to the inorganic phosphates. A batch process suitable for producing trialkoxyalkyl phosphates is disclosed in U.S. Pat. No. 3,020,303 of Pianfetti and Janey. This process includes the steps of reacting a mixture containing from 3–4 moles of an alkali metal hydroxide and about 6 moles of an aliphatic alcohol having from 1–18 carbon atoms per mole of phosphorus oxychloride while concurrently removing substantially all of the water formed in the reaction to produce a substantially anhydrous reaction mixture containing an alkali metal alcoholate, reacting this alcoholate with phosphorus oxychloride at a temperature of about 0°–100° C. to produce a product mixture containing the phosphate ester alcohol and separating the ester from the product mixture while maintaining the reaction to produce both the alcoholate and the final ester in a non-oxidizing atmosphere. Batch operation of this process produced products of good color on the order of 50 on the platinum cobalt scale (ASTM D1209).

This batch process is suitable for producing several different products in the same equipment. Conversion of the batch process to a continuous process produces trialkoxyalkyl phosphates such as tributoxyethyl phosphate of poor color while tributyl phosphate of good color can be made in the same continuous process equipment. The off-color trialkyloxy phosphates can be treated to remove color but it is desirable to avoid such treatment.

The present invention provides a process for the production of alkoxyalkyl triorganic phosphates utilizing a continuous process for the manufacture of alkoxyalkyl alkoxides comprising the steps of treating an alkoxyalkanol with a sodium borohydride ($NaBH_4$) for 20 minutes to 4 hours before the alkoxyalkanol is utilized in the continuous alkoxidation reaction. After the sodium borohydride treatment the alkoxyalkanol, hereafter called the alcohol, is reacted with an alkali metal hydroxide, preferably sodium hydroxide and dehydrated in a continuous reaction to form an alkali metal alkoxide. A large excess of alcohol is employed. The alkoxide is phosphorylated by reaction with phosphorus oxychloride to form a crude trialkoxyalkyl phosphate. The alkoxidation reaction and the phosphorylation reaction are both conducted in a non-oxidizing atmosphere. The crude product is then refined by drowning, i.e. washing with water, to remove the salt reaction product, stripped to remove excess alcohol, washed to remove other unwanted impurities and any remaining salt, and dried to remove residual moisture. The color of the final product is between 25 and 200 platinum cobalt color.

The alcohols useful in this process include the alkoxyalkyl substituted carbinols, i.e. alkoxy alkanols, of the formula $R_1-OR_2OH$ in which $R_1$ contains 1 to 6 carbon atoms and $R_2$ contains 1 to 4 carbon atoms. Included are alkyl alkanols such as 2-methoxyethanol, 2-ethoxyethanol, 2-butoxyethanol, 2-i-propoxyethanol and 2-hexoxyethanol, which mixed carbonols have chain lengths ranging from 2 to 18 carbon atoms.

The alkali metal hydroxides used in this process include sodium, potassium or lithium hydroxides with sodium hydroxide being preferred for economic reasons.

A typical example of the process will be described using 2-butoxyethanol and sodium hydroxide. The 2-butoxyethanol is treated with sodium borahydride for a period of 20 minutes to 4 hours or more. The treated 2-butoxyethanol is then continuously vaporized and fed continuously to a lower section of a dehydration column reactor. Sodium hydroxide is continuously fed as a solution to the top of the column reactor and reacts with the vaporized 2-butoxyethanol which enters near the bottom of the column.

A 2-butoxyethanol-water azeotrope forms near the top of the column and is removed from the top of the column and condensed. The condensed overhead is separated into an organic phase containing the 2-butoxyethanol and an aqueous phase. The aqueous phase (water) is removed from the process and the 2-butoxyethanol is returned to the top of the column. The alkoxide leaving the column reactor assays about 20 to 30% alkoxide and can be concentrated by removing some of the excess alcohol prior to phosphorylation if so desired. Typically, the sodium hydroxide is fed to the column as a concentrated solution, such as a 50% solution. The feed rate of the sodium hydroxide solution and the vaporous alkoxyalkyl substituted carbinols are adjusted to the capacity of the equipment to insure that substantially all of the hydroxide reacts and to remove water from the system. When using a 50% aqueous sodium hydroxide and vaporized 2-butoxyethanol good results are obtained by maintaining a mid-column temperature at about 120° C. Obviously the control point can be located in the column at locations other than the mid-point and different control temperatures would be utilized.

The alkoxide, 2-butoxyethoxide, is then fed to a continuous or batch phosphorylation reaction. In either the continuous or batch mode the process is conducted about as disclosed in U.S. Pat. No. 3,020,303. That is, the alkoxide reaction mixture is cooled to 50° C. or lower, preferably 25° to 50° C. The cooled alkoxide is reacted with phosphorus oxychloride at a rate that maintains the temperature below 100° C., preferably within the range of 30° to 60° C. Faster reaction rates can be used by cooling the reaction mixture. The phosphate ester, such as tri-butoxyethyl phosphate is treated with enough water to dissolve the alkali metal salt. Up to this point the reactions, alkoxidation and phosphorylation are conducted in a nonoxidizing atmosphere but after the salt removal the nonoxidizing atmosphere is no longer necessary. The crude ester is then separated from the salt solution. The crude ester may be purified in any desired manner. For example, the unreacted alcohol can be recovered from the crude by distillation, which alcohol can then be recycled to the process.

The following examples further illustrate the process of this invention. All parts and percentages are by weight unless otherwise noted.

Comparison Example A

A continuous alkoxidation reaction was conducted in a dehydration column reactor capable of reacting sodium hydroxide which is fed at a rate of 11.5 pounds per minute (100% NaOH basis) as a 50% solution while vaporized 2-butoxyethanol is fed near the bottom of the column under a pressure of 60 inches of water (60° F.)

and at a rate to react with substantially all the hydroxide feed. A 300% excess of alcohol is employed. Additional excess alcohol azeotropes with the water in the hydroxide solution and the water produced in the alkoxidation reaction. The azeotrope is removed overhead, condensed and separated into an alcohol phase and a water phase. The water is removed from the process and the alcohol is returned to the process near the top of the dehydration column reactor. The reaction product removed from the bottom of the column reactor assayed 25% sodium butoxyethoxide and contained 0.065% sodium hydroxide when the column midpoint temperature was maintained at 120° C. The sodium 2-butoxyethoxide reaction product was cooled to 50° C. and then reacted slowly with cooling with phosphorus oxychloride in a nitrogen atmosphere while maintaining the temperature of the phosphorylation reaction mixture at 50° C. When phosphorylation was complete sufficient water was added with vigorous agitation to the phosphorylation reaction mixture to give a 20% NaCl solution. The salt solution was separated from the crude phosphate ester reaction mixture. The phosphate ester was distilled to remove the excess alcohol which was recycled to the process. The phosphate ester was washed with a 1% sodium hydroxide solution and washed twice with water. The phosphate ester was then dried and determined to have a color of 150 on the Pt-Co scale (ASTM D1209-79).

Example of the Invention

The procedure of the comparative example was followed except that the 2-butoxyethanol was treated with 250 parts per million of sodium borohydride. The sodium borohydride was added as a stabilized solution containing 12% sodium borohydride, 40% sodium hydroxide and 12% water to the 2-butoxyethanol with stirring and held for 20 minutes before use was started. A 50% aqueous sodium hydroxide solution was fed to the dehydration column reactor at a rate of 8.1 pounds per minute (100% NaOH basis). The sodium borohydride treated 2-butoxyethanol was vaporized at 175° C. and fed to the column at a pressure of 150 inches of water (60' F). The reaction product mixture assayed 25% butylethoxide and contained 0.062% sodium hydroxide. The phosphorylation reaction was conducted and the refined tris butoxyethyl phosphate had a Pt-Co color of 40. The example of this invention was repeated using 100 parts per million of sodium borohydride to treat the 2-butoxyethanol and the color of the trisbutoxyethyl phosphate was 100.

What is claimed is:

1. In the process for making trisubstituted phosphate esters in which six moles of an alkoxyalkanol of the formula $$R_1-O-R_2OH$$

in which $R_1$ contains 1 to 6 carbon atoms and $R_2$ contains 1 to 4 carbon atoms, (a) is continuously reacted with 3 to 4 moles of an alkalimetal hydroxide in a non-oxidizing atmosphere to produce the corresponding alkali metal alkoxide while concurrently removing substantially all of the water formed in said reaction to produce a substantially anhydrous reaction mixture and (b) reacting this reaction mixture with phosphorus oxychloride in a non-oxidizing atmosphere at a temperature in the range of 0° to 100° C. to produce a product mixture containing the product ester of said alcohol and (c) separating the ester from the reaction mixture the improvement which comprises treating the alkoxyalkanol with 100 to 150 parts per million of sodium borohydride for at least 20 minutes before reacting the alkoxyethanol with the alkali metal hydroxide.

2. The process of claim 1 in which the alkoxyalkanol is selected from 2-methoxyethanol, 2-ethoxyethanol, 2-butoxyethanol, 2-i-propoxyethanol and 2-hexoxyethanol.

3. The process of claim 2 in which the alkoxyalkanol is 2-butoxyethanol.

4. The process of claim 2 or 3 in which the sodium borohydride is added to the alkoxyethanol as a solution containing 12% sodium barohydride 40% sodium hydroxide and 48% water.

* * * * *